United States Patent [19]
Lloyd et al.

[11] Patent Number: 5,298,259
[45] Date of Patent: Mar. 29, 1994

[54] SUBUNIT DELIVERY COMPOSITION AND METHOD

[75] Inventors: David H. Lloyd, San Francisco; Robert J. DeFranco, San Carlos, both of Calif.

[73] Assignee: Applied Biosystems, Inc., Foster City, Calif.

[21] Appl. No.: 788,322

[22] Filed: Nov. 5, 1991

[51] Int. Cl.⁵ .......................... A61K 9/10; A61K 9/16; C07K 1/06; B65D 3/26
[52] U.S. Cl. .................................... 424/486; 424/487; 424/501; 514/772.3; 514/772.6; 514/772.4; 524/100; 524/102; 524/103; 935/88; 222/478; 222/485; 222/325
[58] Field of Search .... 424/484, 486, 487, 78.1–78.16; 428/402; 524/100, 102, 103; 530/334; 536/27, 28; 935/88; 525/54.1, 54.11; 521/528

[56] References Cited

U.S. PATENT DOCUMENTS 4,086,302 4/1978 Morgan et al. ...................... 528/398

Primary Examiner—Edward Webman
Attorney, Agent, or Firm—Peter J. Dehlinger; Joseph H. Smith

[57] ABSTRACT

A polymer composition having a biopolymer subunit entrapped in a swellable polymer matrix is described. The composition may be supplied in a disposable cartridge, for use in delivering a solution of the subunit in an automated biopolymer synthesis operation.

17 Claims, 4 Drawing Sheets

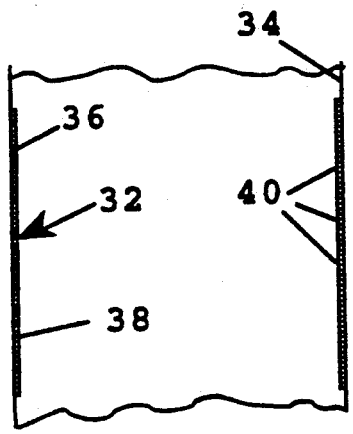
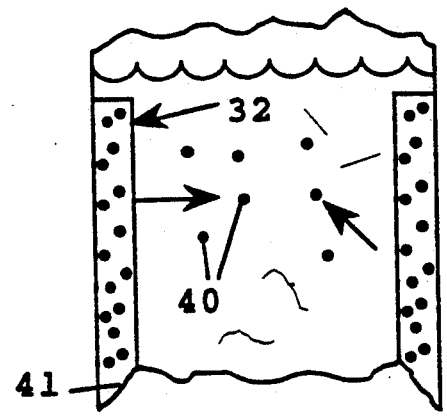
Fig. 2A  Fig. 2B
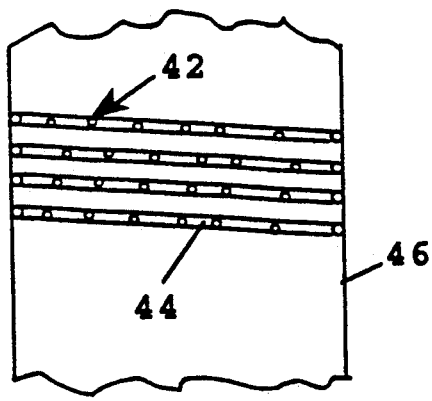
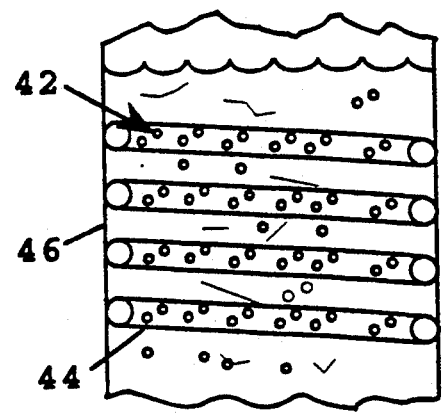
Fig. 3A  Fig. 3B

SUBUNIT DELIVERY COMPOSITION AND METHOD

FIELD OF THE INVENTION

The present invention relates to a composition and method for biopolymer subunit delivery in an automated peptide or oligonucleotide synthesizer.

BACKGROUND

Selected-sequence biopolymers, such as peptides and oligonucleotides, are routinely synthesized by solid-phase methods in which a series of selected polymer subunits are added sequentially to a growing polymer chain covalently attached to a solid support. In a typical peptide synthesis, the peptide is synthesized stepwise from an immobilized C-terminal residue. At each step, a new N-protected amino acid is added in solution to the solid support, and reacted through its free carboxyl group with the free α-amine group of the amino acid (or peptide) immobilized on the support, to couple the new amino acid to the growing peptide on the support. The support is then treated to remove the N-protecting group of the last added amino acid, and the procedure is repeated in a stepwise fashion until the final peptide is complete.

An oligonucleotide, e.g., DNA strand, is similarly synthesized by solid-phase methods, by stepwise addition of a selected 5'-protected nucleotide to a resin containing an immobilized 3'-end nucleoside Backbone coupling is between the free 5' OH group of the immobilized nucleoside, and the activated 3'-end of the free nucleotide. After the coupling reaction, the support is treated to remove the 5'-end protecting group, and the reaction steps are repeated stepwise until the desired-sequence polynucleotide is complete.

Solid-phase methods for peptide and oligonucleotide synthesis can be carried out conveniently by automated synthesizers which are designed for successive addition of selected subunits, coupling agents, and deprotecting agents to a vessel containing the solid-phase material. That is, each subunit addition step involves (a) adding a deprotection solution to the solid-phase vessel, to deprotect the last-added residue on the immobilized support, and (b) adding the next subunit, either in activated form or in the presence of an activator, to the solid-phase vessel, to couple the subunit to the growing polymer chain on the solid support.

In a typical operation of an automated synthesizer, the machine is first loaded with vials containing each of the subunits which are to be added during operation, and with the deprotection and wash solutions used during operation. The vials containing the individual subunits may be prepackaged in liquid form, allowing the subunit solution to be transferred readily from the vial to the solid-phase vessel. Such vials, of course, must be stored in a manner which prevents leakage or breakdown of the subunit or activation components.

Alternatively, the subunit materials may be packaged in the vials in dry form. The dried material is either manually dissolved prior to loading into the machine, or more commonly, is dissolved during machine operation, by addition of a selected volume of solvent to each vial. One limitation of the dry material is that, for many protected amino acids, poor powder flow properties and low bulk density of the material makes the material difficult to measure and package. In addition, some solid protected amino acids dissolve very slowly, requiring up to thirty minutes of contact time with an added solvent before the subunit is fully dissolved. For these reasons, a composition having handling and dissolution properties which are superior to those of the existing available reagents would be useful.

SUMMARY OF THE INVENTION

It is an object of the invention to provide, for use in an automated synthesizer, a biopolymer subunit in a form which can be conveniently and precisely packaged and which allows the biopolymer subunits to be dissolved readily.

In one aspect, the invention includes a polymer composition comprising a dried polymer substrate which is swellable, but insoluble, in an organic solvent and which has an internal polymer matrix. Biopolymer subunit molecules are entrapped within the polymer matrix of the substrate. When the substrate is swelled by contact with an organic solvent, the subunit molecules diffuse out of the matrix into the swelling solvent.

The polymer substrate may be formed of polystyrene, polyacrylate, polymethacrylate, polyacrylamide, polyvinylpyrrolidone, or co-polymers thereof and including polymers having charged, e.g., ammonium or sulfonate groups, attached to the backbone ("ion-exchange resins"), and the polymers are crosslinked with a suitable cross-linking reagent, preferably having a concentration of between 0.5 and 5.0 mole percent. The substrate is preferably capable of swelling in the presence of an organic solvent to a volume which is at least 5–10 times that of the its dry volume.

In one preferred embodiment, the substrate comprises particles which form a flowable mass in a dried state. A preferred particle polymer is polystyrene crosslinked with 1.0% divinylbenzene. The polymer particles preferably contain entrapped biopolymer subunit molecules at a weight ratio of biopolymer subunit to polymer of about 1:10 to 2:1, and the particles containing entrapped biopolymer subunit have a density between about 0.5 and 0.6 g/cc.

In one embodiment, for use in an automated peptide synthesizer, the biopolymer subunit in the composition is an N-protected amino acid or activated derivative. In another embodiment, for use in an automated oligonucleotide synthesizer, the biopolymer subunit in the composition is an activated, 5'-OH protected nucleotide.

In another aspect, the invention includes a cartridge for use in an automated solid-phase synthesis apparatus. The cartridge includes a chamber which contains the polymer composition of the type just described. The cartridge also includes ports for solvent addition and removal, during operation.

The cartridge of the invention is preferably used in an automated solid-phase synthesis apparatus having a solvent-transfer assembly, fittings adapted for connection to the ports, and a pump capable of circulating solvent between the fittings, for carrying out the steps, in an automated procedure, of (a) introducing solvent into the chamber, to cause swelling of the polymer composition and diffusion of the subunit molecules into the solvent, (b) removing the solution of subunit/solvent from the chamber, and (c) introducing the subunit solution into a reaction vessel containing the solid-phase synthesis support.

In another aspect, the invention includes a method for adding biopolymer subunits to a solvent in an automated biopolymer synthesis apparatus. In this method, an organic solvent is added to the polymer composition of the type described above, and the biopolymer subunits are then recovered in the organic phase.

These and other objects and features of the invention will become more fully apparent when the following detailed description of the invention is read in conjunction with the accompanying drawings.

BRIEF DESCRIPTION OF THE DRAWINGS

FIGS. 2A and 2B are schematic illustrations of a composition formed in accordance with another embodiment of the invention, shown before and after swelling by solvent addition;

FIGS. 3A and 3B are schematic illustrations of a composition formed in accordance with another embodiment of the invention, shown before and after swelling by solvent addition;

DETAILED DESCRIPTION OF THE INVENTION

A. Polymer Composition

The composition of the invention is designed as a storage form of a biopolymer subunit, for use in supplying a given amount of the subunit in solution form in an automated biopolymer synthesis apparatus.

Figures 1A, 1B, 1C:
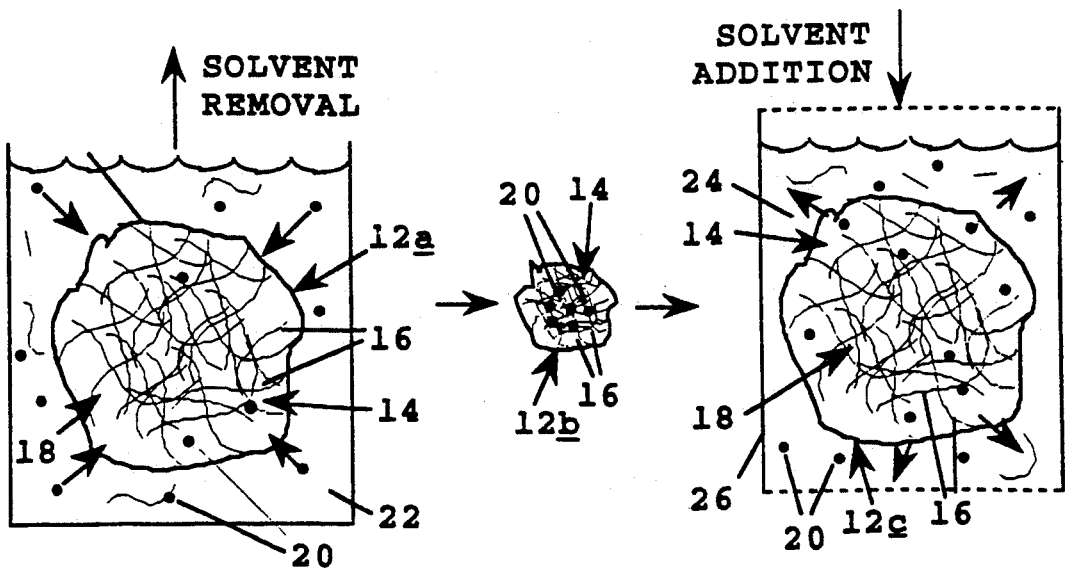
FIGS. 1A-1C are schematic illustrations of a composition particle (1A) during formation by subunit influx and solvent removal, (1B) in a dried, storage state, and (1C) during swelling and release of entrapped subunit (1C)

FIGS. 1A-1C show one particle of a polymer composition formed in accordance with the invention. The particle, which is indicated at 12a, 12b, and 12c in FIGS. 1A-1C, respectively, is formed of a polymer substrate 14 which is swellable in a selected organic solvent, such as N-methylpyrrolidone (NMP), dimethylformamide (DMF), methylene chloride, or tetrahydrofuran (THE) which is suitable for solid-phase subunit addition reactions in biopolymer synthesis. The substrate is formed of cross-linked polymer filaments, such as filaments 16, which form a matrix 18 through which biopolymer subunit molecules, such as subunit molecules 20, can readily diffuse when the substrate is in a swollen state.

A variety of polymers are suitable for use in the invention. These include polystyrene, polyacrylate, polymethacrylate, polyacrylamide, polyvinylpyrrolidone, as well as co-polymers and derivatives thereof. The polymers are lightly cross-linked by inclusion of a cross-linking agent in the polymer composition, preferably at a mole percent of about 0.5-5. One preferred polymeric composition consists of polystyrene crosslinked with 1% divinylbenzene.

More generally, any polymer which, in a cross-linked matrix, is swellable and insoluble in solvents such as DMF, NMP, methylene chloride, or THF used in solid-phase biopolymer synthesis, and which allows for subunit diffusion through the polymer matrix, in a swollen-substrate state, is suitable. Preferably the swollen volume of the polymer (in the swelling solvent) is at least 5-10 times its dried volume.

Polymeric particles which are used in forming the composition serve to increase the overall bulk density and improve flow properties of the dried biopolymer subunit reagent, so that a precise amount of the subunit can be more easily loaded into a vial. One preferred form of the substrate is polymer beads, preferably having diameter size range of a diameter of at least 50 microns, and preferably within the range of 50-200 microns, in dried form. Polystyrene beads having the desired polymer composition, swellability, and particle size, in dried form, are commercially available from Eastman Kodak, BioRad, or Polymer Lab.

FIG. 1A illustrates a method of preparing the composition, i.e., loading the substrate with the biopolymer subunits. A solution of the subunits in a suitable solvent 22, such as one of the organic solvents mentioned above, is mixed with the polymer particles in a mixing vessel. The concentration of particles is such as to form a particle slurry, which may be relatively viscous after the particles have swelled. The concentration of polymer subunits in the solution is selected to produce a final desired weight ratio of subunit/dried substrate preferably between about 1:10 to 2:1. For use with an automated peptide synthesizer, the biopolymer subunits are preferably N-protected amino acids, typically one of the 20 natural L-acids having protected alpha-amine groups, and protected carboxy, hydroxy, thiol, amide and amine side chain groups. For use with an automated oligonucleotide synthesizer, the subunits are typically activated 5'-protected nucleotides, such as one of the four DNA deoxyribonucleoside 3'-phosphoramidites having a 5' dimethoxytrityl (DMT) blocking group.

During formation of the composition, the subunit molecules infiltrate the matrices of the swollen particles, as they equilibrate between the bulk phase of the suspension and the entrapped matrix volume. At the same time, solvent is removed from the particles, forcing progressively more of the subunit molecules into the entrapped volume. Solvent removal is carried out, with agitation, until the particles are completely dried, and substantially all of the subunit is entrapped (or associated with) the particles.

FIG. 1B illustrates a dried particle 12b in the composition, after complete solvent removal. As noted above, particle size in the dried state is preferably between about 50 and 200 microns, and several times more than that in the swollen state. The dried particles have a known amount of subunit per composition weight, and form a flowable particle composition which can be readily transferred, in known weight amounts, from one vessel to another. The preparation of a particle composition containing entrapped fluorenylmethoxycarbonyl (Fmoc) protected L-(alanine) is detailed in Example 1.

FIG. 1C illustrates how the particles in the composition are used in forming a solution of biopolymer subunit molecules, in an automated synthesizer operation. Here a suitable solvent, such as solvent 24, is added to a vial 26 containing the loaded particles, such as particle 12c. As the particles swell in the solvent, subunit molecules entrapped in the particle matrices, such as molecules 20, diffuse into the bulk phase of the solvent. At final equilibrium, the concentration of subunits in the bulk phase medium in the vial is equal to that in the entrapped matrix. Preferably, the total bulk phase volume constitutes at least about 50-80% of the total volume of solvent in the vial, so that at least about 50-80% of the subunit present in the dried composition is recovered in the bulk phase medium. In a typical automated polypeptide synthesis operation, the composition in the vial is designed to supply about 0.075 mmoles protected amino acid in about 1 ml of bulk-phase solution. In a typical automated oligonucleotide synthesis operation, the composition in the vial is designed to supply about 1 μmoles activated nucleotide in 0.5 ml of bulk-phase solution.

Solvents which are suitable for the swelling and extraction step just described include solvents which facilitate swelling of the polymer particles and which are compatible with the synthetic reaction in which the biopolymer subunit is to participate. In one embodiment in which N-α-protected amino acids are added to a peptide synthesis reaction utilizing 9-fluorenylmethyoxycarbonyl (Fmoc) chemistry, a useful solvent is dimethylformamide (DMF). Activating agents useful for polypeptide synthesis may be added to the polymer composition with the solvent. Alternatively, or in addition, protected amino acids can be added in activated forms, such as symmetrical anhydrides, pentafluorophenyl esters and 1-oxo-2-hydroxydihydrobenzotriazine active esters.

An activating agent which can be used in the aforementioned Fmoc based peptide synthesis is hydroxy-O-benzotriazole tetramethyluronium hexafluorophosphate (HBTU), to which is added an equivalent amount of hydroxy-O-benzotriazole (HOBT) and Z equivalents of diisopropylethylamine (DIEA). Other appropriate solvent/activator solutions include dichloromethane (DCM)/dicyclohexyl carbodiimide (DCC) for tertiary-butyloxycarbonyl (t-Boc) based peptide synthesis, dimethylformamide (DMF)/N-methylpyrrolidone (NMP) and (NMP)/dimethyl sulfoxide (DMSO) for Fmoc based peptide synthesis. Other solvent/activator combinations are also possible, and optimal combinations for a given synthetic reaction depend on the type of synthesis and the type of chemical coupling system used in the synthesis.

In a particle composition formed from the abovedescribed polystyrene beads, and containing selected 5'-OH DMT-protected, 3' phosphoramidite deoxyribonucleoside subunit, a useful solvent is acetonitrile. Other appropriate solvents are methylene chloride, and DMF/methylene chloride mixtures.

In a particle composition having a weight ratio of L-amino acid:polymer substrate of 1:2, the time required for equilibration of amino acid into bulk phase for 50 mg of composition suspended in 1 ml of DMF is between about 1 and 5 minutes at room temperature, depending on the particular amino acid and polymer material. After equilibration, the bulk phase medium is removed from the vial, preferably through a filtration medium, for use in a subunit addition reaction in an automated synthesizer, as described below.

FIGS. 2A and 2B illustrate a composition 32 formed in accordance with another embodiment of the invention. In this embodiment, the composition has a film-like polymer substrate 36 which forms a lining or coating 38 on the sides of a vial 34. The substrate contains entrapped subunit molecules, such as molecules 40, and has a polymer composition similar to that of the composition described above. The substrate lining has a thickness, in dried form preferably between about 25–100 microns. The substrate is loaded with a selected amount of subunit, as above, by solvent removal from a solution of the subunit in a solvent capable of swelling the polymer.

FIG. 2B illustrates the condition of composition 32 during subunit release, when a suitable reaction solvent 41 is added to the vial. As the substrate swells in the added solvent, the entrapped subunit molecules diffuse through the substrate matrix and into the bulk-phase medium, until equilibrium is achieved. The resulting subunit solution is then drawn off for use in a subunit addition reaction.

FIGS. 3A and 3B illustrate a composition 42 formed in accordance with a third embodiment of the invention. In this embodiment, the composition has a filament-like substrate 44, which may be attached to the walls of a vial 46, as indicated. The substrate, which contains entrapped subunit molecules, has a polymer composition similar to that described above. The filament thickness, in dried form is preferably between about 25–200 microns. The substrate is loaded with subunit molecules as above. FIG. 3B illustrates the composition after substrate swelling and subunit release, for use in preparing a subunit solution for solid-phase biopolymer synthesis.

B. Cartridge

Figure 4:
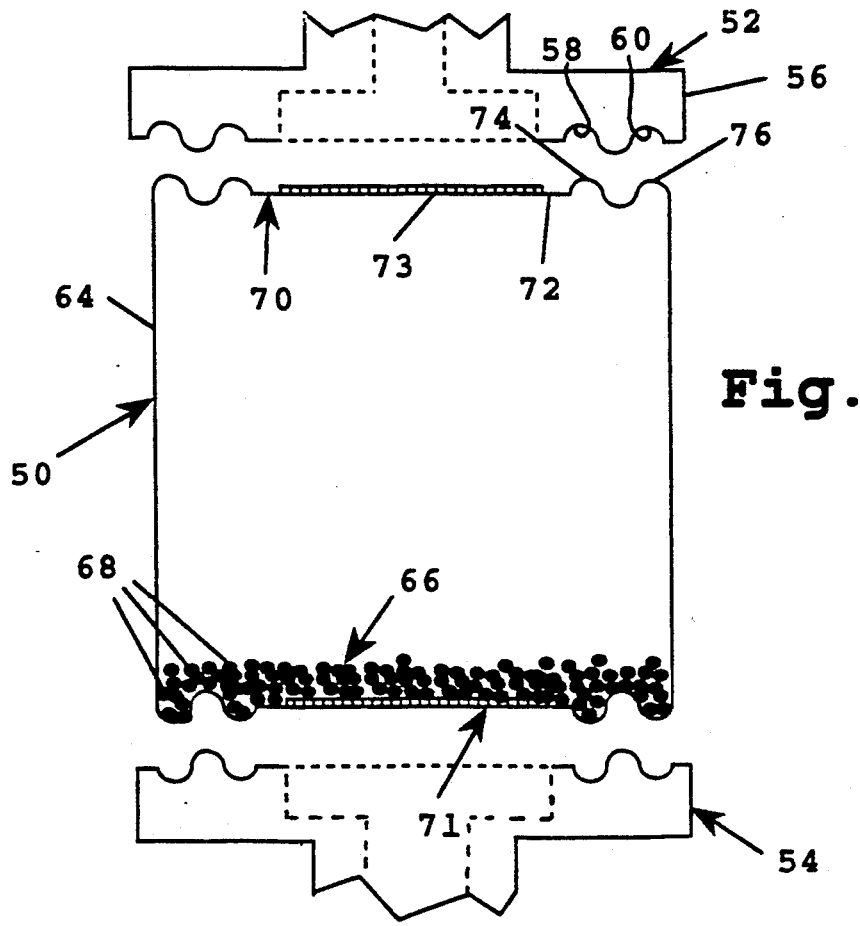
FIG. 4 shows a cartridge constructed according to the invention, containing a dried polymer particulate composition, such as shown at FIG. 1B.

In another aspect, the invention includes a cartridge for use in an automated solid-phase synthesis apparatus, for delivering a selected amount of biopolymer subunit in solution form to a subunit-addition reaction chamber. One exemplary cartridge is shown at 50 in FIG. 4. The cartridge is designed to be engaged automatically by a pair of fittings 52, 54 in the synthesis apparatus, to connect the vial in line with a fluid-transfer assembly in the apparatus, for transferring fluid into and from the vial, as discussed below. Fitting 52, which is representative, includes a head 56 having a pair of annular grooves 58, 60 which form part of a fluid seal, when the fitting is engaged with the cartridge. The seal is formed by moving the two fittings toward one another to positions of sealing engagement with the cartridge.

Cartridge 50 includes a vial or container 64 which defines an internal chamber containing a polymer composition, such described in Section A. In the embodiment shown, the composition is a particle composition 66 composed of dried polymer particles, such as particles 68. It will be appreciated that other polymer compositions, such as the film- or filament-type compositions described above, are also suitable. A typical cartridge has a container volume of about 0.5 ml, and contains about an amount of subunit corresponding to about 0.075 mmoles of amino acid subunit, or about 1 μmole of activated nucleotide. The container is preferably formed of polyethylene or similar resilient inert plastic.

The cartridge is provided with inlet and outlet ports, or port means, 70, 71 through which solvent is introduced into and removed from of the cartridge, respectively. Inlet port 70, which is representative, is formed by a central opening 72 in an end of the container, covered by a porous membrane 73 which is effective to filter particles, in either dried or swelled form, and allow solvent passage through the filter. The ends of the vial, such as the end confronting fitting 52, are provided with a pair of annular ridges, such as ridges 74, 76 which mesh with the annular grooves of the confronting fitting, to form a fluid-tight seal, when the fitting is moved into sealing position.

It will be appreciated that a film- or filament-type composition which is anchored to the vial walls may not require a filter membrane to contain the composition within the vial before and after swelling. Further, the port means may include a single port for receiving a fitting that serves both to supply and remove solvent from the container. A variety of conventional port and fitting constructions, effective to form a seal in a contact position may be employed, and the particular port and fitting constructions shown are only exemplary.

C. Automated Biopolymer Synthesizer

Figure 5:
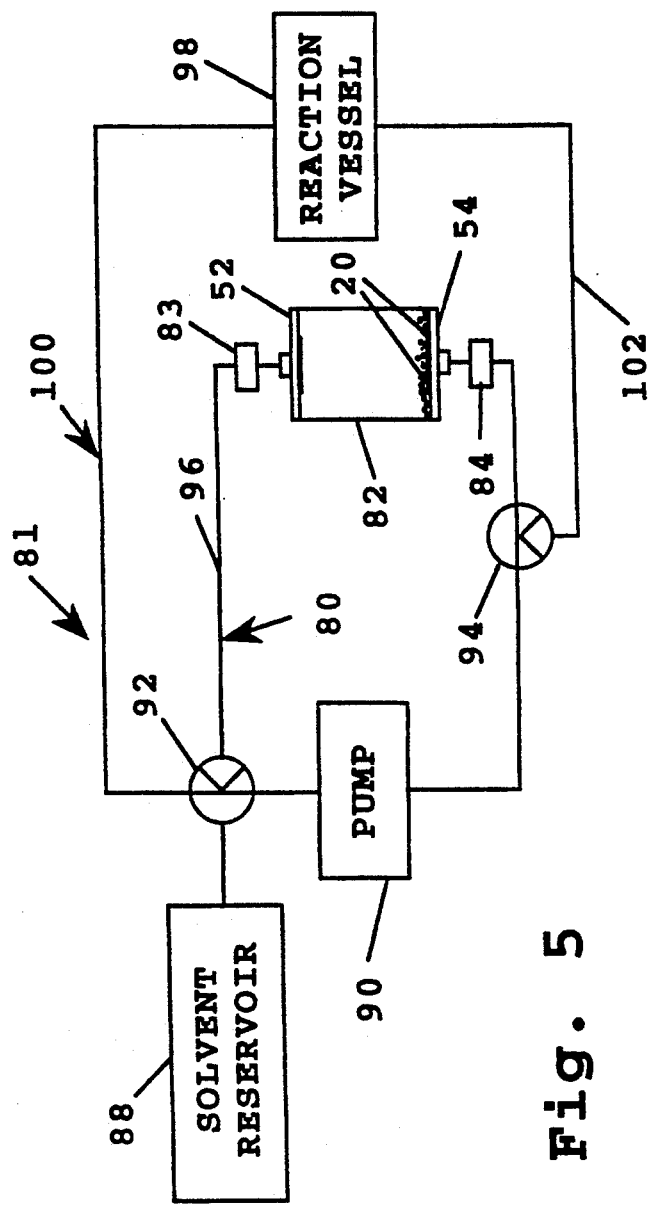
FIG. 5 schematically illustrates a solvent-transfer assembly and an attached cartridge, such as shown in FIG. 4, in an automatic peptide synthesizer.

FIG. 5 is a schematic view of elements of a solvent-transfer device 80 in an automated synthesizer apparatus 81. The assembly is designed for transferring solvent to and from a cartridge, such as cartridge 82 described in FIG. 4, during operation of the synthesizer. Included in the assembly are fittings 52, 54, as described above, and suitable means, such as indicated at 83, 84, for moving the fittings toward and away from a solvent-transfer position, shown in the figure, in which the fittings are in sealing engagement with opposite cartridge ends.

Also included in the assembly are a solvent reservoir 88, a pump 90, and a pair of valves 92, 94 connecting the pump, reservoir and fittings as shown, by solvent-feed lines, such as line 96. Also in the solvent-transfer assembly is a reaction vessel 98 which communicates with valve 92 through a feed line 100, and with valve 94, through a feed line 102. The two valves are switchable to positions connecting various pairs of feed lines, as indicated in the figure.

Figure 6:
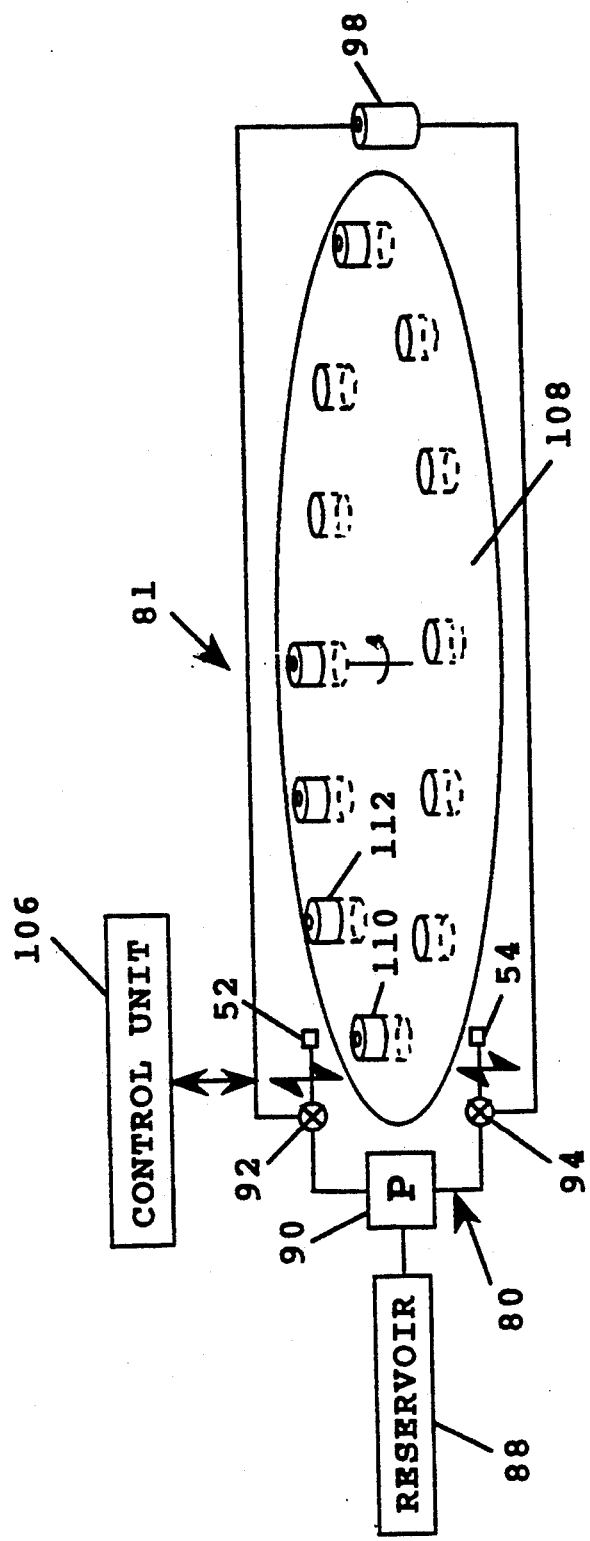
FIG. 6 shows the solvent transfer assembly and associated carousel in an automated synthesizer constructed according to the present invention.

The pump, valves and fittings in assembly 80 are under the control of a microprocessor control unit 106, shown in FIG. 6. The design and operation of the control unit will be readily understood from the operation of the apparatus described below.

FIG. 6 is a partially schematic view of portions of apparatus 81, showing the solvent-transfer assembly just described and a carousel 108 designed to hold different-subunit cartridges, such as cartridges 110, 112, used in biopolymer synthesis. The carousel is operable, under the control of unit 106, to place a selected cartridge in position for connection to fittings 52, 54, for solvent transfer into and from the cartridge.

In operation, the carousel is loaded with cartridges containing different selected peptide or oligonucleotide subunits, and a suitable solid-phase material is placed in reaction chamber 98. The solid-phase material is pre-swollen and washed, either before or after loading into the reaction chamber. At the first subunit addition cycle, a selected cartridge, such as cartridge 110, is positioned between fittings 52, 54, and fittings are moved to a position engaging the ends of the cartridge. Valves 94, 96 are now set to positions in which pump 90 draws solvent from reservoir 88 into the cartridge through fitting 52, and out of the cartridge through fitting 54, until a selected volume of liquid has been drawn out of the reservoir. Upon contact of the solvent with the polymer composition in the vial, the cartridge begins to swell and release subunit molecules into the solvent. The solvent may include an activating agent or other reagent suitable for achieving coupling of the released subunit onto a growing biopolymer chain in the reaction vessel.

When the desired amount of solvent has been drawn from the reservoir, valve 94 is switched to a position which allows the solvent in the cartridge to circulate in the loop which includes both valves. The solvent is circulated through the cartridge typically for 5-10 minutes, until the subunit molecules in the composition reaches equilibrium between polymer matrix and bulk-phase volumes, as discussed above. At this point, the valves are switched to pump the bulk-phase subunit solution from the cartridge into reaction vessel 98. The subunit solution is allowed to react in the vessel for a period sufficient for subunit coupling.

After completion of the coupling reaction, the fluid contents of the reaction vessel are aspirated as solvent waste, and additional solvent mixtures, such as a wash solution, and deprotection solution are separately added to the reaction vessel, according to conventional synthesizer operation. The carousel is then moved to position the cartridge such as cartridge 112 containing the next-in-sequence subunit, and the subunit addition cycle described above is repeated. These steps are repeated until the desired sequence biopolymer is synthesized.

D. Subunit Supply Method

It can be appreciated from the foregoing that the invention includes a method of supplying or delivering a biopolymer subunit in a biopolymer synthesis procedure. The method includes adding a solvent to a polymer composition of the type described in Section A, allowing the polymer substrate to swell sufficiently to release the subunit molecules into the solvent, and separating the solvent containing the subunit molecules from the polymer particles.

These steps are preferably carried out in a cartridge similar to the one described in section B above, in an automated synthesizer, as described in Section C.

From the foregoing, it will be appreciated how various objects and features of the invention are met. The composition provides a convenient storage form of protected biopolymer subunits which is (a) easily prepared, at a desired weight ratio of subunit to polymer substrate, (b) readily weighed and transferred as a flowable mixture, for preparing a disposable cartridge, and (c) rapidly dissolved upon contact with a suitable reaction solvent.

The following example illustrates a specific amino acid composition for use in a solid-phase synthesizer, in accordance with the present invention.

EXAMPLE 1

Preparation of Amino Acids in Swellable Polymeric Matrices

An N-$\alpha$-protected (Fmoc) L-(alanine) obtained from Bachem, Inc. (Switz) was dissolved in tetrahydrofuran (THF) at a concentration of 167 mg/ml. To 1200 ml of this solution was added 200 g of polystyrene particles, 100-200 mesh (75-150 microns nominal diameter), obtained from Eastman Kodak (#41240; Rochester, N.Y.) to form a particle slurry. The slurry was first stirred without vacuum for 1 hour to insure complete absorption, then stirred under vacuum until complete solvent removal was achieved. The dried mass was then broken up in a jar mill and sieved to a free flowing mass. The particle characteristics are summarized in Table 1.

TABLE 1

| Property | Unfilled | Filled |
|---|---|---|
| Bulk density (g/mL) | 0.62 | 0.57 |
| amino acid content (% dry weight) | 0 | 50 |

Although the invention has been described with respect to specific embodiments and examples, it will be appreciated that various changes and modification may be made without departing from the invention.

It is claimed:

1. A polymer composition for adding a solution of a biopolymer subunit in a biopolymer synthesis operation, comprising
    a dried polymer substrate which (i) is swellable, but insoluble in an organic solvent, and (ii) has an internal polymer matrix through which molecules of the biopolymer subunit can diffuse when the substrate is in a swollen state; and
    molecules of the biopolymer subunit entrapped within the matrix, such that suspension of the substrate in such organic solvent produces swelling of the substrate and diffusion of the subunit molecules through the matrix and into the solvent, where the biopolymer subunit is selected from the group consisting of an N-protected amino acid and an activated 5'-protected nucleotide.

2. The composition of claim 1, wherein the substrate is composed of a cross-linked polymer selected from the group consisting of polystyrene, polyacrylate, polymethacrylate, polyacrylamide, polyvinylpyrrolidone, and co-polymers thereof.

3. The composition of claim 2, wherein the volume of the substrate, in a swollen state, is at least about 5–10 times that in the dried state.

4. The composition of claim 3, wherein the substrate is composed of a polymer and a crosslinking agent present at a mole percent of between 0.5 and 5.

5. The composition of claim 1, wherein the substrate comprises swellable polymer particles have sizes between about 50 and 200 microns.

6. The composition of claim 5, wherein the particles are flowable in dried form.

7. The composition of claim 1, wherein the substrate comprises a filament having a filament diameter, in the dried state, between about 25–200 microns.

8. The composition of claim 1, wherein the substrate comprises a planar polymer film having a thickness, in the dried state, between about 25–200 microns.

9. The composition of claim 1, wherein the biopolymer subunit is an N-protected amino acid.

10. The composition of claim 9, wherein the N-protected amino acid is activated at its carboxyl end for reaction with a free amine group.

11. The composition of claim 1, wherein the biopolymer subunit is an activated, 5'-OH protected nucleotide.

12. The composition of claim 1, which has a weight ratio of biopolymer subunit to polymer of about 1:10 to 2:1.

13. A cartridge for an automated solid-phase synthesis apparatus, where said cartridge is designed to use biopolymer subunit molecules supplied in cartridge form, comprising
    means defining a chamber which is adapted to be connected to said apparatus;
    port means for introducing a solvent into and removing a solvent from the chamber; and
    contained within the chamber, a polymer composition comprising (a) a dried polymer substrate which (i) is swellable in an organic-phase solvent and (ii) has an internal polymer matrix through which subunit molecules can diffuse when the substrate is in a swollen state, and (b) molecules of said biopolymer subunit entrapped within the matrix, such that suspension of the substrate in said solvent produces swelling of the substrate and diffusion of the subunit molecules through the matrix and into the solvent, where the biopolymer subunit is selected from the group consisting of an N-protected amino acid and an activated 5'-protected nucleotide.

14. A method of adding a solution of a biopolymer subunit to a solid-phase reagent in an automated biopolymer synthesis apparatus, comprising
    adding an organic solvent to a dried polymer substrate having a matrix in which molecules of the subunit are entrapped, and through which the molecules can diffuse, when the substrate is in a swelled state, where the biopolymer subunit is selected from the group consisting of an N-protected amino acid and an activated 540 -protected nucleotide; and
    recovering the organic solvent bulk phase containing biopolymer subunit molecules from the polymer matrix.

15. The method of claim 14, wherein the biopolymer subunit is an N-protected amino acid.

16. The method of claim 14, wherein the biopolymer subunit is an activated, 5'-protected deoxyribonucleotide.

17. The method of claim 14, wherein the organic solvent contains an activating agent.

* * * * *